United States Patent [19]

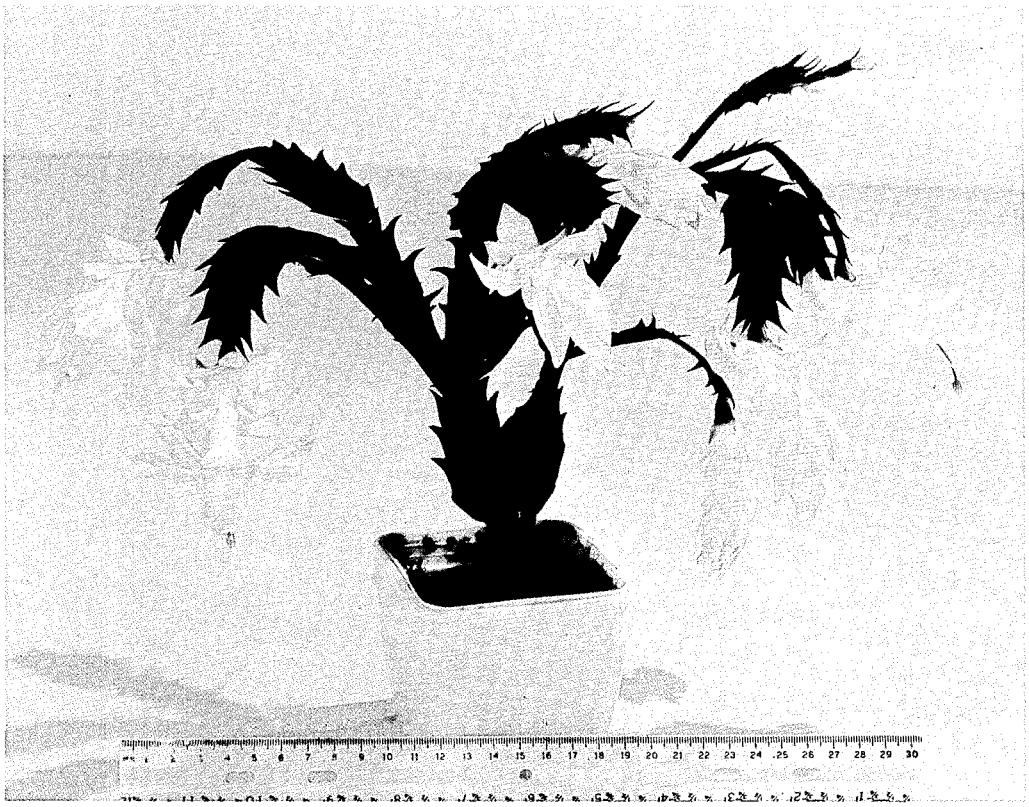

Cobia et al.

[11] Plant 4,201

[45] Jan. 24, 1978

[54] CACTACEAE PLANT

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,432

[22] Filed: Jan. 18, 1977

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family has a generally "purplish" colored bloom with the color in the marginal blade areas of the perianth tube laminating and forming series of tepals being dominated by a reddish purple hue. The tepals of the bloom have generally greater width dimensions in comparison to correspondingly located tepals of the 'Lavender Doll' variety and those of the perianth tube laminating series emerge generally closer to the distal end of the perianth tube than those of the 'Lavender Doll' variety so that the bloom in comparison is fuller and with a more compact tepal arrangement. The life of the bloom ranges from about 6 to about 9 days. The stems in comparison to the 'Lavender Doll' variety, have fewer branches, generally longer phylloclades and somewhat thicker wings.

2 Drawing Figures

1

The invention relates to a new and distinct plant variety of the Cactaceae family and which has been named the *Zygocactus truncatus* 'Lavender Lady' by the inventors.

Certain plant varieties of the Cactaceae family are well known in the foliage plant market and among these are the various varieties of the *truncatus* species of the Zygocactus genus that bloom in the months of November and December in the Northern Hemisphere and hence are commonly called "Christmas Cactus".

One such well known variety is that known as the "Violaceae" variety. This variety has a "purplish" colored bloom that is appealing to purchasers during the Thanksgiving-Christmas holiday seasons. The bloom life however varies from 3 to about 6 days and the variety suffers from the disadvantage that many of the flower buds which start to mature fail to reach maturity and instead drop from the stems. Growers, are accordingly reluctant to grow this variety because of transportation delays and the large costs that are involved in manually selecting specimens for shipment which are at the proper stage of budding to provide reasonable assurance of mature blooming when the specimens reach their destination. The variety is also generally considered to be a "slow grower" and it has a low tolerance to nutrient deficiencies and a resistance to fungus type diseases which is less than satisfactory to many growers.

Yet another variety of the *truncatus* species with a "purplish" colored bloom is that known as the *Zygocactus truncatus* 'Lavender Doll' variety and which has only recently appeared in the marketplace during the past few years. This variety forms the subject matter of U.S. Plant Pat. No. 3,690 and has a greater resistance to bud abscission, a greater tolerance to nutrient deficiencies and fungus type diseases as well as a faster growth rate than the 'Violaceae' variety. The 'Lavender Doll' variety also has a more acceptable bloom life than that of the 'Violaceae' variety.

The 'Lavender Doll' variety has a heritage which is traceable to the variety commonly known as "Christmas Cheer". This latter variety has what may be called a "salmon" color that is considered by some to be less appealing during the Thanksgiving-Christmas season

2 than some of the other bloom colors appearing on related varieties. However its tolerances to nutrient deficiencies, bud abscission and fungus type diseases are greater than the 'Violaceae' variety, and its bloom life usually ranges from about 5 to about 8 days.

A general objective of the invention has been to develop a variety of the Cactaceae family with a so-called "purplish" colored bloom that has a fuller appearance and more compact tepal arrangement than exhibited by the 'Violaceae' and 'Lavender Doll' varieties. Yet another objective of the invention has been to develop a variety having the foregoing general objective as well as an acceptable bloom life.

The objectives of the invention have been fully realized by the development of the new plant variety hereinafter described in detail. The new plant variety was developed in a nursery located in Winter Garden, Fla., as a hybrid secured by cross pollinating the flower of a hybrid plant specimen having a heritage on the paternal side that include the "Christmas Cheer" variety with pollen from a plant specimen of another variety that was developed from a vegetative mutation that appeared on a hybrid variety which has a heritage that includes both the "Christmas Cheer" and 'Violaceae' varieties. Both paternal varieties are research varieties that have not appeared in the marketplace with the maternal variety having a white bloom characteristic while the paternal variety has a lavender bloom characteristic. The seeds taken from the fertilized seed pod were cultivated at the mentioned nursery location and after prolonged observation of the seedlings, the hybridized plant of the new plant variety was selected and asexually reproduced by the inventors at the Winter Garden nursery location by the propagation of stem cuttings taken from the original hybrid plant.

Through successive propagations, it has been ascertained that specimens of the new plant variety generally resemble the parent varieties but are distinguishable from these varieties and from other related varieties known to the inventors by a growth habit which is evident in plant specimens propagated and grown under nursery conditions utilized in the growing of tropical plants at Winter Garden, Florida, as combining the following principal characteristics:

1. A generally "purplish" colored bloom with a color in the marginal blade areas of the perianth tube laminating and forming tepal series being dominated by a reddish purple hue.

2. A bloom with tepals having generally greater width dimensions in comparison to correspondingly located tepals of the 'Lavender Doll' variety and including perianth tube laminating tepals which emerge generally closer to the distal end of the perianth tube than those of the 'Lavender Doll' variety, whereby the bloom in the new variety appears fuller and with a more compact tepal arrangement than exhibited by the 'Lavender Doll' variety, 3. A bloom with a perianth tube that is basically translucent white and/or in color dominated by yellowish pink and/or purplish pink hues, 4. A bloom life of from about 6 to about 9 days, and 5. Stems having fewer branches and generally longer phylloclades with thicker wings in comparison to those of the 'Lavender Doll' variety.

The accompanying drawings serve by color photographic means, to illustrate the new plant variety and wherein one sheet is a color photograph of a plant specimen with a fully opened bloom and buds in earlier stages of maturity and the other sheet generally illustrates the bloom and its characteristics.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The description is further based on observations of well fertilized plants of less than one year of age from initial propagation and which were grown under 50–70% shaded glasshouse nursery conditions in the Winter Garden, Fla. area and wherein temperatures range from 60° to 85° F. during the winter months, from 75° to 95° F. during the summer months and are ambient during intervening periods.

DETAILED PLANT DESCRIPTION

Name: *Zygocactus truncatus* 'Lavender Lady'.

Parentage:

*Maternal.*—Unnamed and unmarketed hybrid variety with a white bloom having a heritage that include the variety of the *truncatus* species known commercially as "Christmas Cheer."

*Paternal.*—Unnamed and unmarketed variety having a lavender bloom color characteristic and developed from a mutation that appeared on a hybrid plant specimen of a variety having a heritage that includes *Zygocactus truncatus* 'Violaceae' and the *Zygocactus truncatus* variety known commercially as "Christmas Cheer."

Classification:

*Botanic (Britton and Rose, The Cactaceae, Constable and Co., Ltd., London* 1937, *Vol IV).*—

| | |
|---|---|
| (1) Family: | *Cactaceae* |

-continued

| | |
|---|---|
| (2) Tribe: | *Cereeae* |
| (3) Sub-tribe: | *Epiphyllanae* |
| (4) Genus: | *Zygocactus* |
| (5) Species: | *truncatus* (Haworth) Schumann |

*Commercial.*—Thanksgiving-Christmas blooming cactus.

Form: Terrestrial, shade-loving, succulent, leafless plant with jointed and branched stems.

Stems:

*General.*—Irregular with usually mono-chotomous to di-chotomous branching of upright, adventitiously rootable, flattened phylloclades that have a prominent midrib and prominently toothed lateral wings.

*Phylloclades.*—General: Elongated and flat with transversely elongated, areole bearing, truncated apex, with inwardly tapering basal wing margins that merge through a broad, usually pointed, basal juncture with the phylloclade therebelow, and with an axillary areole associated with each tooth. Midrib: General — Extends longitudinally of phylloclade and continuously through joints with laterally tapering cortex at wing insertions. Pith surrounding vascular bundles that branch and provide lateral extensions of the vascular system to marginal teeth. Texture — Smooth, waxy epidermis with wax in small embedded scales and becoming corky in basal stem areas with age. Size (2–6 mos. old) — Length: Usually between 49 and 75 mm. with the average for respective plant specimens being usually between 55 and 65 mm. Thickness: Usually between 2.2 and 5.5 mm. with the average for respective plant specimens being usually between 3.1 and 5.0 mm. Color (at maturity) — Commonly moderate yellow green (5 GY 5/6) (5 GY 5/4) (7.5 GY 5/6) (near 7.5 GY 5/4) and/or moderate olive green (near 5 GY 4/4) (near 7.5 GY 4/6) (near 7.5 GY 4/4) (7.5 GY 3/4). Wings: General shape — Generally flattened from midrib cortex to tooth insertions with slight thinning taper toward margins. Margins — Toothed (modified leaves). Texture — Succulent to leathery with smooth waxy epidermis having wax arranged in small embedded scales and becoming corky in basal plant areas with age. Size (2–6 mos. old) — Center thickness: Usually between 1.3 and 3.6 mm. Width (as measured from phylloclade axis to most offset lateral areole): Usually between 8 and 15 mm. Color (at maturity) — Commonly moderate yellow green (5 GY 5/4) (7.5 GY 5/4), grayish olive green (near 7.5 GY 4/3) and/or moderate olive green (near 5 GY 4/4) (7.5 GY 4/4) (near 7.5 GY 4/3) ( 7.5 GY 3/4). Teeth: General shape — Generally flattened and tapering along margins from wing insertion to an apex having a hyaline, single cell, pointed spine with nonpredictable bending. Adaxial marginal shape: Generally straight but with both concave and convex adaxial marginal tendencies. Abaxial marginal shape: Irregular with tendencies toward a medial indentation that provides a distal terminus for a convex proximal marginal edge portion and a basal terminus for a distal marginal edge portion that varies from straight to convex. Orientation — Usually projects generally distally of phylloclade base in an alternate arrangement and with the tooth angles (as measured at the distal side of the intersect with the phylloclade axis of a line through the tooth apex and the midpoint between the abaxial and adaxial areoles thereof, formed by the nonbasal teeth of a phylloclade usually being between 30° and 46°. Margins — Entire. Texture — Succulent to leathery with smooth waxy epidermis having wax in small embedded scales and becoming corky in basal plant areas with age. Number — Usually from 8 to 11 per phylloclade. Size (2–6 mos. old) — Center thickness: Usually between 0.6 and 1.9 mm. Areole to apex dimension (adaxial marginal side): Usually between 5 and 13 mm. for teeth located distally of basal teeth. Color (at maturity) — Commonly moderate olive green (near 5 GY 4/4) (near 7.5 GY 7/4) (7.5 GY 3/4) and/or moderate yellow green (5 GY 5/4) (7.5 GY 5/4). Areoles: Terminal areole — Large, elongated, oval-shaped with several acicular bristles, copious multi-cellular hairs, and several buds that may mature into either new phylloclades or flowers. The opposite ends of the areole are located adjacent to subsidiary areoles which are in turn located at the axils of teeth that are located at the distal end of phylloclade. Axillary areoles — Acicular bristles without glochidia but having copious, short, brownish to colorless, multi-cellular hairs. Areoles are commonly found in the basal portion of the phylloclade in association with a vestigial tooth that is less than 1 mm. in length. (Vestigial teeth not considered in teeth number or length of teeth)

Buds: Unarmored, ovid and chlorophyllous.

Flowers:

*General.*—Sessile, zygomorphic, usually solitary, terminal, perfect and epigynous with double hypanthium and tepals (undifferentiated whorled sepals and tepals) having a spiral emergence as a perianth provided with a sepaloid series of free tepals, a tube laminating series of tepals, and a tube forming series of united tepals.

*Sepaloid series.*— General: Free tepals inserted on top of ovary. Shape: Deltoid in outer members of whorl and grading inwardly on the whorl to tepals which are usually either obovate or ovate and less frequently elliptical. Tips are broadly acuminate with some acute tendencies, and margins are entire with sparse irregular teeth appearing mainly in the apex areas. Texture: Succulent and glabrous outer whorl members and grading inwardly in the whorl to silken blades with fleshy basal areas. Number: Usually from 7 to 12. Size (at full bloom): Base-tip dimension — Usually less than 37 mm. Maximum width dimension — Usually less than 23 mm. Color: It varies from the smallest to the largest tepals in outer whorl members with the smallest tepal usually having a continuous field that in color has a yellow green hue while the largest tepal usually has a marginal blade area which in color is dominated by a reddish purple and/or purplish pink hue and a center field which in color is dominated by a yellow green hue. Commonly brilliant yellow green (2.5 GY 8/8), light yellow green (near 2.5 GY 8/6), strong yellow green (2.5 GY 7/8) (5 GY 7/8) and/or moderate yellow green (5 GY 7/6) in the continuous field of the smallest tepal and in the center field of the largest tepal of the outer whorl. Commonly light reddish purple (10 P 6/8) (10 P 6/6) (2.5 RP 6/8) (2.5 RP 6/6), moderate purplish pink (5 RP 7/8) (7.5 RP 7/8) and/or dark purplish pink (7.5 RP 6/8) in the marginal blade areas of the largest tepal in the outer whorl. The inner whorl tepals have a center field which in color is dominated by purplish pink, pink, yellowish pink and/or yellow green hues and marginal areas which in color are dominated by reddish purple, and/or purplish pink hues. Commonly pale purplish pink (5 RP 9/2), purplish white (5 RP 9/1), pale pink (5 R 9/2), pale yellowish pink (10 R 9/2) and/or pale yellow green (10 Y 9/2) (2.5 GY 9/2) and/or (5 GY 9/2) in the center field of the inner whorl members. Commonly light reddish purple (10 P 6/8) (10 P 6/6) (2.5 RP 6/8) (2.5 RP 6/6), moderate purplish pink (5 RP 7/8) (7.5 RP 7/8) and/or dark purplish pink (7.5 RP 6/8) in marginal areas of inner whorl members. Orientation at full bloom: Varying inwardly in the whorl from outer members, which are erect to acute, to inner whorl members which are perpendicular to heavily recurved.

*Tube liminating series.*—General: Tepals inserted on ovary and basally united below the throat as outer laminations on the perianth tube and with progressively greater amounts of basal fusion inwardly in the whorl. Shape: Grading inwardly in the whorl with progressively longer base-tip dimensions and with blade areas changing inwardly from obovate to broadly elliptical and with acute tips. Entire margins with sparse irregular teeth mainly in apex areas. Texture: Succulent, slightly fleshy basal areas with silken blades. Number: Usually between 2 and 6. Size (at full bloom): Base-tip dimension — Usually between 31 and 63 mm. Maximum width dimension — Usually between 18 and 28 mm. Color: Tepals with basal areas that in color are translucent white and/or dominated by purplish pink and/or pink hues and with marginal areas that are dominated by reddish purple hues. Commonly pale purplish pink (5 RP 9/2) and/or pale pink (5 R 9/2) in the basal areas and commonly light reddish purple (10 P 6/8) (10 P 6/6) (2.5 RP 6/8) (2.5 RP 6/6), strong reddish purple (10 P 5/10) and/or moderate reddish purple (10 P 5/8) in marginal blade areas. Orientation (at full bloom): Acute to recurved.

*Tube forming series.*— General: Tepals basally united to form hollow perianth tube that is inserted on ovary and equipped with irregular carina (keel) at throat. Shape: Perianth tube — Elongated and ellipsoidal to oval in cross section. Blades — Generally elliptic to broadly elliptic with obovate tendencies and with acuminate tips. Entire margins with sparse, irregular teeth mainly in apex area. Carina (keel) — Transcending and irregular. Texture: Perianth tube — Thick, succulent and slightly ribbed. Blades — Translucent and silken. Carina (keel) — Fleshy. Blade Number: Usually 8. Size (at full bloom): Perianth tube — Base to keel length: Usually between 32 and 38 mm. along axis of tube with average length differences between measurements along dorsal and ventral sides for respective specimens usually being between 2 and 5 mm. Internal major axis (at throat): Usually between 9 and 14 mm. when measured perpendicular to axis of perianth tube. Internal minor axis (at throat): Usually between 5 and 10 mm. when measured perpendicular to axis of perianth tube. Blades — Length (keel to tip): Usually between 28 and 37 mm. Width (maximum): Usually between 16 and 23 mm. Color (at full bloom): Perianth tube — Translucent white and/or dominated by pink, yellowish pink and/or purplish pink hues. Commonly translucent white, pale yellowish pink (10 R 8/2), pale pink (5 R 9/2), pale purplish pink (5 RP 9/2). Blades — Translucent white basal areas that extend distally in the blade and merge with marginal blade areas that in color are dominated by a reddish purple hue. Commonly strong reddish purple (10 P 5/10) (2.5 RP 5/10) and/or moderate reddish purple (10 P 5/8) (2.5 RP 5/8) in the marginal blade areas. Carina (keel) — Commonly moderate reddish purple (near 2.5 RP 4/8), strong reddish purple (2.5 RP 4/10), deep reddish purple (2.5 RP 3/10) (2.5 RP 3/8) and/or dark purplish red (5 RP 3/8) (5 RP 3/6). Orientation (at full bloom): Erect to slightly recurved.

*Androecium (stamens).* — General: Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. Stamen number: Tube attached group — Usually between 70 and 85. Basally united group — Usually between 19 and 22. Filaments: General — Translucent and glabrous with anther connective. Shape — Long, slender and gradually tapering from base to anther connective. Texture — Glabrous and silken. Color — A translucent white. Size (at full bloom) — Length: Tube attached group — Usually between 40 and 58 mm. Basally united group — Usually between 45 and 58 mm. Diameter: Usually between 0.25 and 0.4 mm. intermediate the opposite ends. Anthers: General — Adnate with four longitudinally dehiscent pollen sacs. Shape — Elongated. Texture — Waxy. Color (post dehiscence or pollen color) — Usually light greenish yellow (7.5 Y 9/6) and/or pale greenish yellow (7.5 Y 9/4) (10 Y 9/4).

*Gynoecium (pistil).* — General: Compound, parietal placentation with united style surrounded by annular diffuse nectary at its insertion. Style: General — Stout and inserted in ovary. Shape — Elongated and terrete. Texture — Fleshy and glabrous with short inner glutinous hairs at distal end. Color — Commonly purplish pink and/or reddish pink hue at proximal end and blending distally with color dominated by a purplish red hue at the distal end. Commonly moderate purplish pink (10 P 7/8), deep purplish pink (near 5 RP 6/10), light reddish purple (10 P 6/8) (2.5 RP 6/8) (2.5 RP 6/6) and/or strong reddish purple (10 P 5/10) (2.5 RP 5/10) at the proximal ends and moderate purplish red (7.5 RP 4/8) (10 RP 4/8) and/or (10 RP 4/10) at the distal end. Size (at full bloom) — Length: Usually between 61 and 68 mm. Diameter: Usually between 0.7 and 1.3 mm. intermediate the opposite ends. Stigma: General — Exserted and erect with usually 6 inner marginally adhering lobes. Shape — Elongated and tapering toward lobe tips and having relatively blunt apices. Texture — Fleshy and smooth with short glutinous hairs. Color — Commonly strong reddish purple (10 P 5/10) (2.5 RP 5/10) and/or moderate purplish red (5 RP 5/10). Size (lobe length at full bloom) — Usually between 3.5 and 6.5 mm. Ovary: General — Epigynous with thin epidermis and distally located concavity and with single cavity having usually 6 carpels with numerous ovules. Shape — Terrete to ovoid and generally broadening from insertion to floral end. Texture — Succulent and glabrous with thin outer epidermis. Color — Commonly dark greenish yellow (near 7.5 Y 6/6) (10 Y 6/6), light olive green (10 Y 6/4) (10 Y 5/6) (near 10 Y 5/4) and/or moderate yellow green (2.5 GY 6/6) (2.5 GY 6/4). Size (at full bloom) — Length (insertion to concavity base): Usually between 8.5 and 11 mm. Major axis (distal end of concavity): Usually between 7.5 and 11 mm. Minor axis (distal end of concavity): Usually between 6 and 9.5 mm.

Growing characteristics: A fast growth rate nearly approaching that of the 'Lavender Doll' variety with resistances to nutrient deficiencies, fungus type diseases and bud absission that are comparable to those of the 'Lavender Doll' variety. Stems with fewer branches and generally longer phylloclades with thicker wings in comparison to those of the 'Lavender Doll' variety and a bloom that appears fuller and with a more compact tepal arrangement than exhibited by the 'Lavender Doll' and 'Violaceae' varieties and which is attributed to greater tepal overlap in the bloom and to an emergence of the tube laminating tepals generally closer to the distal end of the perianth tube than those of the 'Lavender Doll' and 'Violaceae' varieties and with a bloom life (from initial tepal separation to initial tepal withering) of from about 6 to about 9 days.

The following is a general description of a specimen of the new plant variety that was grown from the propagation of a single phylloclade in a nursery at Winter Garden, Fla.

Age of plant: 12 months from initial propagation. Plant was pruned after 5 months to a level of growth one tier above the original cutting.

Branches from propagated cutting: 2.

Branches formed after pruning: 5.

General (branch numbers refer to branches from the original cutting:

| Branch No. | No. of Phylloclades | Max. Length | No. of Tips |
|---|---|---|---|
| 1 | 10 | 228 mm. | 3 |
| 2 | 11 | 244 mm. | 4 |

Midribs:

| Branch No. | Length (avg.) | Thickness (avg.) |
|---|---|---|
| 1 | 58 mm. | 4.8 mm. |
| 2 | 61 mm. | 3.9 mm. |

Wings:

| Branch No. | Center Thickness (avg.) | Max. Width (avg.) |
|---|---|---|
| 1 | 1.7 mm. | 10 mm. |
| 2 | 1.7 mm. | 12 mm. |

Teeth:

| Branch No. | No./Phylloclades (avg.) | Center Thickness | Areole to Apex Dimension (avg.) | Tooth Angle (avg.) |
|---|---|---|---|---|
| 1 | 9 | 1.14 mm. | 9.1 mm. | 40° |
| 2 | 9.5 | 1.26 mm. | 8.8 mm. | 36° |

Phylloclade color: Grayish olive green (near 7.5 GY 4/3), and moderate olive green (7.5 GY 4/4) (near 5 GY 4/4).

The following is a general description of a flower of the new plant variety which bloomed in December on a plant grown under shaped glasshouse nursery conditions in Winter Garden, Fla.

Bloom life: 8 days.

Sepaloid series of tepals:

*Number.*—7.

*Size (at full bloom).*—Maximum base-tip dimension: 28 mm. Minimum base-tip dimension: 5 mm. Maximum width dimension: 22 mm.

*Color.*—Strong yellow green (2.5 GY 7/8) and moderate yellow green (5 GY 7/6) in continuous field of smaller tepals and in median area of largest tepals in outer whorl. Moderate purplish pink (5 RP 7/8) and (7.5 RP 7/8) in marginal areas of largest tepals in outer whorl members. Pale yellow green (2.5 GY 9/2) in median areas of intermediate sepaloid tepals and moderate purplish pink (5 RP 7/8) (7.5 RP 7/8) in marginal areas of intermediate tepals. Pale pink (5 R 9/2) and pale yellowish pink (10 R 9/2) in median areas of inner tepals and moderate purplish pink (5 RP 7/8) (7.5 RP 7/8) and dark purplish pink (7.5 RP 6/8) in marginal areas of innermost tepals.

Tube laminating series:

*Number.*—5.

Size (at full bloom).—Maximum base-tip dimension: 51.5 mm. Minimum base-tip dimension: 32 mm. Maximum width dimension: 25 mm. Minimum width dimension: 20.5 mm.

*Color.*—Pale pink (5 R 9/2) and translucent white (neutral 9.5/0) in basal and median areas. Strong reddish purple (10 P 5/10) and moderate reddish purple (10 P 5/8) in marginal blade areas.

Tube forming series of tepals:

*Number.*—8.

*Size (at full bloom).*—Perianth tube: Base to keel length — 37 mm. Interior major axis (at throat) — 13 mm. Interior minor axis (at throat) — 9 mm. Blades: Maximum length (keel to tip) — 35 mm. Minimum length (keel to tip) — 30 mm. Maximum width — 22 mm. Minimum width — 17 mm.

*Color.*—Perianth tube: Pale yellowish pink (10 R 9/2). Blades: Translucent white in basal and median area and strong reddish purple (10 P 5/10) (2.5 RP 5/10) in marginal blade areas. Carina (keel): Strong reddish purple (2.5 RP 4/10) and deep reddish purple (2.5 RP 3/10) (2.5 RP 3/8).

Androecium:

*Stamen number.*—Tube attached group: 81. Basally united group: 20.

*Filaments.*—Color: Translucent white. Size (at full bloom): Length — Tube attached group: 52 mm. (average). Basally united group: 51 mm. (average). Diameter — About 0.3 mm. intermediate the opposite ends.

*Anthers.*—Color (post dehiscence): Pale greenish yellow (7.5 Y 9/4).

Gynoecium (pistil):

*Style.*—Color: Light reddish purple (10 P 6/8) (2.5 RP 6/8) in proximal area and moderate reddish purple (10 RP 4/10) in the distal area. Size (at full bloom): Length — 65 mm. Diameter — 0.9 mm. intermediate the opposite ends.

*Stigma.*—Color: Strong reddish purple (10 P 5/10) (2.5 RP 5/10). Size (lobe length): About 4 mm.

*Ovary.*—Color: Moderate yellow green (2.5 GY 6/6) and dark greenish yellow (10 Y 6/6). Size (at full bloom): Length (insertion to concavity base) — 10.5 mm. Major axis (distal end of concavity — 9.5 mm. Minor axis (distal end of concavity) — 8 mm.

We claim:

1. The new and distinct plant variety of the Cactaceae family as described and illustrated and which has a growth habit providing specimens that combine the following principal distinguishing characteristics:

1. A generally "purplish" colored bloom with the color in the marginal blade areas of the perianth tube laminating and forming series of tepals being dominated by reddish purple hue,
2. A bloom with tepals having generally greater width dimensions in comparison to correspondingly located tepals of the 'Lavender Doll' variety and including perianth tube laminating tepals which emerge generally closer to the distal end of the perianth tube than those of the 'Lavender Doll' variety, whereby the bloom of the new variety appears fuller and with a more compact tepal arrangement than exhibited by the 'Lavender Doll' variety,
3. A bloom with a perianth tube that is basically translucent white and/or in color dominated by yellowish pink and/or purplish pink hues,
4. A bloom life of from about 6 to about 9 days,
5. Stems having fewer branches and generally longer phylloclades with thicker wings in comparison to those of the 'Lavender Doll' variety.

* * * * *

UNITED STATES PATENT AND TRADEMARK OFFICE

CERTIFICATE OF CORRECTION

PATENT NO. : Plant No. 4,201

DATED : January 24, 1978

INVENTOR(S) : Barnell L. Cobia and Stephen H. Griffith

It is certified that error appears in the above-identified patent and that said Letters Patent are hereby corrected as shown below:

Col. 3, Line 52, before "Maternal" insert -- A. --; Line 56, before "Paternal" insert -- B. --; Line 64, before "Botanic" insert -- A. --; Col. 4, Line 7, before "Commercial" insert -- B. --; Line 12, before "General" insert -- A. --; Line 17, before "Phylloclades" insert -- B. --; Line 17, before "General" insert -- [1] --; Line 23, before "General" insert -- [2] --; Line 23, before "Midrib" insert -- (a) --; Line 28, before "Texture" insert -- (b) --; Line 31 before "Size" insert -- (c) --; Line 31, before "Length" insert -- (1) --; Line 34, before "Thickness" insert -- (2) --; Line 37, before "Color" insert -- (d) --; Line 41, before "Wings" insert -- [3] --; Line 42, before "General shape" insert -- (a) --; Line 44, before "Margins" insert -- (b) --; Line 45, before "Texture" insert -- (c) --; Line 48, before "Size" insert -- (d) --; Line 49, before "Center Thickness" insert -- (1) --; Line 50, before "Width" insert -- (2) --; Line 52, before "Color" insert -- (e) --; Line 57, before "Teeth" insert -- [4] --; Line 57, before "General shape" insert -- (a) --; Line 60, before "Ad-" insert -- (1) --; Line 63, before "Abaxial marginal shape" insert -- (2) --; Line 68, before "Orientation" insert -- (b) --; Col. 5, Line 8, before "Margins" insert -- (c) --; Line 8, before "Texture" insert -- (d) --; Line 12, before "Number" insert -- (e) --; Line 13, before "Size" insert -- (f) --; Line 13, before "Center thickness" insert -- (1) --; Line 14, before "Areole to apex dimen-" insert -- (2) --; Line 17, before "Color" insert -- (g) --; Line 20, before "Areoles" insert -- [5] --; Line 20, before "Terminal" insert -- (a) --; Line 28, before "Axillary areoles" insert -- (b) --; Line 38, before "General" insert -- A. --; Line 45, before "Sepaloid series" insert -- B. --; Line 45, before "General" insert -- [1] --; Line 46, before "Shape" insert -- [2] --; Line 52, before "Texture" insert -- [3] --; Line 55, before "Number" insert -- [4] --; Line 56, before "Size" insert -- [5] --; Line 56, before "Base-tip dimension" insert -- (a) --; Line 57, before "Maximum width dimension" insert -- (b) --; Line 58 before "Color" insert -- [6] --; Col. 6, Line 23, before "Orientation at full" insert -- [7] --; Line 28, before "Tube laminating

UNITED STATES PATENT AND TRADEMARK OFFICE

CERTIFICATE OF CORRECTION

PATENT NO. : Plant No. 4,201

DATED : January 24, 1978

INVENTOR(S) : Barnell L. Cobia and Stephen H. Griffith

It is certified that error appears in the above-identified patent and that said Letters Patent are hereby corrected as shown below:

series" insert -- C. --; Line 28, before "General" insert -- [1] --; Line 32, before "Shape" insert -- [2] --; Line 37, before "Texture" insert -- [3] --; Line 39, before "Number" insert -- [4] --; Line 39, before "Size" insert -- [5] --; Line 40, before "Base-tip dimension" insert -- (a) --; Line 41, before "Maximum width dimension" insert -- (b) --; Line 42, before "Color" insert -- [6] --; Line 52, before "Orientation" insert -- [7] --; Line 54, before "Tube forming series" insert -- D. --; Line 54, before "General" insert -- [1] --; Line 57, before "Shape" insert -- [2] --; Line 57, before "Perianth tube" insert -- (a) --; Line 59, before "Blades" insert -- (b) --; Line 62, before "Carina" insert -- (c) --; Line 63, before "Texture" insert -- [3] --; Line 63, before "Perianth tube" insert -- (a) --; Line 64, before "Blades" insert -- (b) --; Line 65, before "Carina" insert -- (c) --; Line 66, before "Blade Number" insert -- [4] --; Line 66, before "Size" insert -- [5] --; Line 67, before "Perianth tube" insert -- (a) --; Line 67, before "Base to keel length" insert -- (1) --; Col. 7, Line 4, before "Internal major axis" insert -- (2) --; Line 6, before "Internal minor axis" insert -- (3) --; Line 9, before "Blades" insert -- (b) --; Line 9, before "Length" insert -- (1) --; Line 10, before "Width" insert -- (2) --; Line 11, before "Color" insert -- [6] --; Line 11, before "Peri-" insert -- (a) --; Line 16, before "Blades" insert -- (b) --; Line 23, before "Carina" insert -- (c) --; Line 27, before "Orientation" insert -- [7] --; Line 29, before "Androecium" insert -- E. --; Line 29, before "General" insert -- [1] --; Line 36, before "Stamen number" insert -- [2] --; Line 37, before "Tube attached group" insert -- (a) --; Line 38, before "Basally united group" insert -- (b) --; Line 39, before "Filaments" insert -- [3] --; Line 39, before "General" insert -- (a) --; Line 40, before "Shape" insert -- (b) --; Line 42, before "Texture" insert -- (c) --; Line 43, before "Color" insert -- (d) --; Line 43, before "Size" insert -- (e) --; Line 44, before "Length" insert -- (1) --; Line 44, before "Tube attached group" insert -- (a) --; Line 45, before "Basally united group" insert -- (b) --;

UNITED STATES PATENT AND TRADEMARK OFFICE

CERTIFICATE OF CORRECTION

PATENT NO. : Plant No. 4,201

DATED : January 24, 1978

INVENTOR(S) : Barnell L. Cobia and Stephen H. Griffith

It is certified that error appears in the above-identified patent and that said Letters Patent are hereby corrected as shown below:

Line 46, before "Diameter" insert -- (2) --; Line 48, before "Anthers" insert -- [4] --; Line 48, before "General" insert -- (a) --; Line 50, before "Shape" insert -- (b) --; Line 50, before "Texture" insert -- (c) --; Line 50, before "Color" insert -- (d) --; Line 54, before "Gynoecium" insert -- F. --; Line 54, before "General" insert -- [1] --; Line 56, before "Style" insert -- [2] --; Line 57, before "General" insert -- (a) --; Line 57, before "Shape" insert -- (b) --; Line 58, before "Texture" insert -- (c) --; Line 60, before "Color" insert -- (d) --; Col. 8, Line 1, before "Size" insert -- (e) --; Line 2, before "Length" insert -- (1) --; Line 3, before "Diameter" insert -- (2) --; Line 4, before "Stigma" insert -- [3] --; Line 5, before "General" insert -- (a) --; Line 6, before "Shape" insert -- (b) --; Line 8, before "Texture" insert -- (c) --; Line 9, before "Color" insert -- (d) --; Line 13, before "Size" insert -- (e) --; Line 14, before "Ovary" insert -- [4] --; Line 14, before "Gen-" insert -- (a) --; Line 18, before "Shape" insert -- (b) --; Line 19, before "Texture" insert -- (c) --; Line 21, before "Color" insert -- (d) --; Line 24, before "Size" insert -- (e) --; Line 25, before "Length" insert -- (1) --; Line 26, before "Major" insert -- (2) --; Line 28, before "Minor axis" insert -- (3) --; Col. 9, Line 33, before "Number" insert -- (1) --; Line 34, before "Size" insert -- (2) --; Line 34, before "Maximum base-tip dimension" insert -- (a) --; Line 35, before "Minimum base-tip dimension" insert -- (b) --; Line 36, before "Maximum width dimension" insert -- (c) --; Line 37, before "Color" insert -- (3) --; Line 52, before "Number" insert -- (1) --; Line 53, before "Size" insert -- (2) --; Line 53, before "Maximum base-tip dimen-" insert -- (a) --; Line 54, before "Minimum base-tip dimension" insert -- (b) --; Line 55, before "Maximum width dimension" insert -- (c) --; Line 55, before "Mini-" insert -- (d) --; Line 57, before "Color" insert -- (3) --; Line 62, before "Number" insert -- (1) --; Line 63, before "Size" insert -- (2) --; Line 63, before "Perianth tube" insert -- (a) --; Line 63, before "Base to keel" insert -- (1) --; Line 64, before "Interior major axis"

UNITED STATES PATENT AND TRADEMARK OFFICE

CERTIFICATE OF CORRECTION

PATENT NO. : Plant No. 4,201

DATED : January 24, 1978

INVENTOR(S) : Barnell L. Cobia and Stephen H. Griffith

It is certified that error appears in the above-identified patent and that said Letters Patent are hereby corrected as shown below:

insert -- (2) --; Col. 10, Line 1, before "Interior minor axis" insert -- (3) --; Line 2, before "Blades" insert -- (b) --; Line 2, before "Maximum length" insert -- (1) --; Line 3, before "Minimum length" insert -- (2) --; Line 4, before "Maximum width" insert -- (3) --; Line 4, before "Minimum width" insert -- (4) --; Line 6, before "Color" insert -- (3) --; Line 6, before "Perianth tube" insert -- (a) --; Line 7, before "Blades" insert -- (b) --; Line 10, before "Carina" insert -- (c) --; Line 14, before "Stamen number" insert -- (1) --; Line 14, before "Tube attached group" insert -- (a) --; Line 14, before "Basally united group" insert -- (b) --; Line 16, before "Filaments" insert -- (2) --; Line 16, before "Color" insert -- (a) --; Line 16, before "Size" insert -- (b) --; Line 17, before "Length" insert -- (1) --; Line 17, before "Tube attached group" insert -- (a) --; Line 18, before "Basally united group" insert -- (b) --; Line 19, before "Diameter" insert -- (2) --; Line 21, before "Anthers" insert -- (3) --; Line 21, before "Color" insert -- (a) --; Line 24, before "Style" insert -- (1) --; Line 24, before "Color" insert -- (a) --; Line 26, before "Size" insert -- (b) --; Line 27, before "Length" insert -- (1) --; Line 27, before "Diameter" insert -- (2) --; Line 29, before "Stigma" insert -- (2) --; Line 29, before "Color" insert -- (a) --; Line 30, before "Size" insert -- (b) --; Line 31, before "Ovary" insert -- (3) --; Line 31, before "Color" insert -- (a) --; Line 32, before "Size" insert -- (b) --; Line 33, before "Length" insert -- (1) --; Line 34, before "Major axis" insert -- (2) --; Line 35,

UNITED STATES PATENT AND TRADEMARK OFFICE

CERTIFICATE OF CORRECTION

PATENT NO. : Plant No. 4,201
DATED : January 24, 1978
INVENTOR(S) : Barnell L. Cobia and Stephen H. Griffith It is certified that error appears in the above-identified patent and that said Letters Patent are hereby corrected as shown below:

before "Minor axis" insert -- (3) --;

Signed and Sealed this

*Thirteenth* Day of *November 1979*

[SEAL]

*Attest:*

RUTH C. MASON
*Attesting Officer*

LUTRELLE F. PARKER
*Acting Commissioner of Patents and Trademarks*